(12) United States Patent
Nabel et al.

(10) Patent No.: US 6,780,406 B1
(45) Date of Patent: Aug. 24, 2004

(54) INHIBITION OF VASCULAR SMOOTH MUSCLE CELL PROLIFERATION ADMINISTERING A THYMIDINE KINASE GENE

(75) Inventors: Elizabeth G. Nabel, Ann Arbor, MI (US); Gary J. Nabel, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1826 days.

(21) Appl. No.: 08/210,902

(22) Filed: Mar. 21, 1994

(51) Int. Cl.$^7$ .......................... A01N 63/00; A61K 48/00
(52) U.S. Cl. .......................... 424/93.2; 514/44; 424/450
(58) Field of Search ................................ 424/93.2, 450; 514/44; 935/62; 435/172.3, 240.2, 320.1; 604/96

(56) References Cited

FOREIGN PATENT DOCUMENTS

WO        WO9510623        4/1995

OTHER PUBLICATIONS

Mullen et al., PNAS USA, vol. 89, pp. 33–37, Jan. 1992.*
Chapman et al., Circ. Res., vol. 71 (1) pp. 27–33, Jul. 1992.*
Herbomel et al., Cell, vol. 39, pp. 653–662, Dec. 1984 (Pt 2).*
Morishita et al., PNAS USA, vol. 90, pp. 8474–8478, Sep. 1993.*
Mulligan, Science, vol. 260 pp. 926–932, May 14, 1993.*
Willard et al., Circulation, Supp I, vol. 86 (4), Abstract 1880, Oct. 1992.*
Haj–Ahmad et al., J. Virol., vol. 57(3), p267–274, Jan. 1986.*
Takeshita et al., Circulation, Supp.I, vol. 86(4), Abstract 0903, Oct. 1992.*
Takeshita et al., Circulation, Supp. I, vol. 86(4), Abstract 3179, Oct. 1992.*
Santoian et al., Circulation, Supp. I, vol. 86(4) Abstract 3187, Oct. 1992.*
Ledley, Human Gene Therapy, vol. 2, pp. 77–83, 1991.*
Casscells, W., et al. (1992) Elimination of smooth muscle cells in experimental restenosis: targeting of fibroblast growth factor receptors, Proc. Natl. Acad. Sci. 89:7159–7163.
Guzman, R., et al., (1993) Efficient and selective adenovirus–mediated gene transfer into vascular neointima. Circulation 88(6):2838–2848.
Mazur. W., et al. (1994) Coronary restenosis and gene therapy. Coronary Restenosis and Gene Therapy 21(1):104–111.
Ohno, T., et al., (1994) Gene therapy for vascular smooth muscle cell proliferation after arterial injury. Science 265:781–784.

Takeshita, S., et al. (1994) Increased gene expression after liposome–mediated arterial gene transfer associated with intimal smooth muscle cell proliferation. J. Clin. Invest. 93:652–661.
Venkatesh, L., et al. (1990) Selective induction of toxicity to human cells expressing human immunodeficiency virus type 1 tat by a conditionally cytotoxic adenovirus vector. Proc. Natl. Acad. Sci. 87:8746–8750.
Barr, et al., "Efficient Catheter–Mediated GeneTransfer into the Heart Using Replication–Defective Adenovirus", *Gene Therapy*, 1:51–58 (1994).
Culver, et al., "In Vivo Gene Transfer with Retroviral Vector–Producer Cells for Treatment of Experimental Brain Tumors", *Science*, 256:1550–1552, Jun., 1992.
Curiel, et al., "Adenovirus Enhancement of Transferrin–Polylysine–Mediated Gene Delivery", *Proc. Natl. Acad. Sci. USA*, 88:8850–8854, Oct. 1991.
Davidson, et al., "A Model System for In Vivo Gene Transfer into the Central Nervous . . . ", *Nature Genet.*, 3:219–223 (1993).
Elion, et al., "Selectivity of Action of an Antiherpetic Agent, 9–(2–Hydroxyethoxymethyl) Guanine", *Proc. Natl. Acad. Sci.*, 74:12:5716 (1977).
Lee, et al., "In Vivo Adenoviral Vector–Mediated Gene Transfer into Balloon–Injured Rat Carotid Arteries", *Circulation Research*, 73:5:797–807, Nov., 1993.
Lemarchand, et al., "Adenovirus–Mediated Transfer of a Recombinant Human α–Antitrypsin cDNA to Human Endothelial Cells", *Proc. Natl. Acad. Sci. USA*, 89:6482–6486, Jul. 1992.
Lemarchand, et al., "In Vivo Gene Transfer and Expression in Normal Uninjured Blood Vessels Using Replication–Deficient Recombinant Adenovirus Vectors", *Circulation Research*, 72:5:1132–1138, May 1993.
Mansour, et al., "Disruption of the Proto–Oncogene Int–2 in Mouse Embryo–Derived Stem Cells: A General Strategy for Targeting Mutations to Non–Selectable Genes", *Nature*, 336:348–352, Nov., 1988.
Moolten, et al., "Lymphoma Regression Induced by Ganciclovir in Mice Bearing a Herpes Thymidine Kinase Transgene", *Human Gene Therapy*, 1:125–134 (1990).
Plautz, et al., "Selective Elimination of Recombinant Genes in Vivo with a Suicide Retroviral, Vector", *The New Biologist*, 3:7:709–715, Jul., 1991.

(List continued on next page.)

*Primary Examiner*—Deborah Crouch
(74) *Attorney, Agent, or Firm*—Brinks Hofer Gilson & Lione

(57) ABSTRACT

A method for inhibiting restenosis associated with mechanical injury of a blood vessel. An adenoviral vector encoding a suicide gene such as thymidine kinase is directly administered to the injured vessel followed by treatment with a nucleotide analog. The analog is phosphorylated and converted to a cytotoxin by the suicide gene product, resulting in destruction of the rapidly dividing neointimal cells.

7 Claims, 3 Drawing Sheets

OTHER PUBLICATIONS

Rakugi, et al., "Induction of Angiotensin Converting Enzyme in the Neointima After Vascular Injury", *J. Clin. Invest.,* 93:339–346, Jan., 1994.

Simons, et al., "Antisense C–Myb Oligonucleotides Inhibit Intimal Arterial Smooth Muscle Cell Accumulation in Vivo", *Nature,* 359:67–70, Sep. 1992.

Smith, et al., A New Nucleoside Analog, 9[[2–Hydroxy–1–(Hydroxymethyl)Ethoxy]Methyl]Guanine, Highly Active in Vitro Against Herpes Simplex Virus Types 1 and 2, *Antimicrobial Agents and Chemotherapy,* 22:1:55–61, Jul., 1982.

Stratford–Perricaudet, et al., "Evaluation of the Transfer and Expression in Mice . . . ", *Human Gene Therapy,* 1:241–256 (1990).

\* cited by examiner

INHIBITION OF VASCULAR SMOOTH MUSCLE CELL PROLIFERATION ADMINISTERING A THYMIDINE KINASE GENE

FIELD OF THE INVENTION

The present invention relates to the inhibition of vascular smooth muscle cell proliferation using a polynucleotide encoding a "suicide" gene. When expressed intracellularly, and stimulated by a second compound, the product of the suicide gene kills proliferating cells.

BACKGROUND OF THE INVENTION

The response to arterial injury in vivo is mediated by a complex set of cellular interactions involving endothelial and smooth muscle cells. Following damage to the arterial wall, growth factors and cytokines are released locally and induce cellular proliferation through autocrine and paracrine mechanisms. A common and clinically significant setting for such injury is balloon angioplasty wherein blood vessels narrowed by atherosclerotic deposits are opened using an inflatable balloon. Dilation of the occluded vessel can result in a reactive cellular proliferative response which leads to renarrowing (restenosis) of the arterial lumen. Blood flow is compromised by hyperplasia of the intimal (adjacent to the lumen) layer of the artery and to deposition of extracellular matrix components. Restenosis occurs in approximately 30% of coronary artery angioplasties, thereby presenting a major roadblock to the successful treatment of cardiovascular disease.

A number of approaches for controlling smooth muscle cell proliferation following angioplasty have been attempted, including angiotensin converting enzyme (ACE) inhibitors and antisense RNA directed against cell cycle control proteins (Rakugi et al., (1994) *J. Clin. Invest.*, 93:339–346; Simons et al., (1992) *Nature*, 359:67–70). Although these pharmacological approaches have been somewhat effective in preventing the neointimal hyperplasia associated with balloon angioplasty in a rat carotid model, the application of these approaches to human disease has been unsuccessful.

Replication-deficient adenoviral vectors have been used in a number of promising approaches to gene therapy. Lemarchand et al. demonstrated transfer of the β-galactosidase and $\alpha_1$-antitrypsin genes into the endothelium of normal arteries and veins in sheep using an adenoviral vector (*Circulation Res.*, 5:1132–1138, 1993; *Proc. Natl. Acad. Sci. USA*, 89:6482–6486, 1992). Lee et al. (*Circulation Res.*, 73:797–807, 1993) demonstrated adenoviral vector-mediated transfer of the β-galactosidase gene into balloon-injured rat carotid arteries. These vectors have also been used to transduce mouse hepatocytes in vivo (Stratford-Perricaudet et al., (1990), *Hum. Gene Ther.*, 1:241–256). In addition, expression of a recombinant β-galactosidase gene has been observed after infusion of an adenoviral vector into rabbit coronary arteries (Barr et al., (1994) *Gene Therapy*, 1:51–58).

Culver et al. (*Science*, 256:1550–1552, 1992) injected murine fibroblasts expressing the herpes simplex virus thymidine kinase (HSV-tk) gene into rats with a cerebral glioma. The rats were then given the nucleoside analog ganciclovir (GCV). Once GCV entered the cells expressing the HSV-tk gene, it was phosphorylated by the newly expressed thymidine kinase. Cellular kinases can also phosphorylate GCV, which is incorporated into replicating DNA (Smith et al., (1982) *Antimicrob. Agents Chemother.*, 22:55–61) and causes premature chain termination. As this process inhibited DNA replication, only the actively dividing cells were killed. In this experiment the gliomas regressed completely both microscopically and macroscopically. Other nucleoside analogs capable of being modified by thymidine kinase, such as acyclovir (Elion et al., (1977) *Proc. Natl. Acad. Sci. U.S.A.*, 74:5716–5720), have been used as targets for suicide inhibition of cellular replication.

Moolten et al. (*Hum. Gene Ther.*, 1:125–134, 1990) induced lymphomas with Abelson leukemia virus in transgenic mice carrying the HSV-tk gene. Following treatment of 12 mice with GCV, 11 exhibited complete tumor regression.

Plautz et al. demonstrated in vivo regression of a transplantable murine adenocarcinoma transfected with a HSV-tk gene and treated with GCV. In these same experiments, expression of a HSV-tk-β-galactosidase construct in nondividing rabbit arterial cells was unaffected by GCV treatment, demonstrating the selectivity of this approach in the maintenance of quiescent cells and the elimination of rapidly dividing cells in vivo (Plautz et al., (1990) *New Biologist*, 3:709–715).

The efficacy of introducing a suicide gene into smooth muscle cells has not been previously addressed. For this reason, there exists a need for safe, effective methods of inhibiting neointimal hyperplasia after mechanical vessel injury. The present invention provides a solution to this need.

SUMMARY OF THE INVENTION

One embodiment of the present invention is a method for inhibiting restenosis associated with mechanical treatment of a blood vessel in a mammal comprising:

introducing a polynucleotide encoding a thymidine kinase gene to the blood vessel after mechanical treatment;

expressing the thymidine kinase gene to produce thymidine kinase protein in cells of the blood vessel; and then administering to said mammal an effective amount of a DNA replication-inhibiting nucleoside analog capable of being phosphorylated by the thymidine kinase protein and preferentially incorporating the phosphorylated analog into the DNA of proliferating cells, whereby the proliferating cells are killed.

Preferably, the mechanical treatment is balloon angioplasty, laser, atherectomy device or stent implantation and the thymidine kinase gene is in a eukaryotic expression vector. More preferably, the expression vector is a viral vector. Most preferably, the viral vector is an adenoviral vector. In another aspect of this preferred embodiment, there is provided a polyoma virus enhancer, adenoviral vector enhancer elements, encapsidation signals and an origin of replication separate from said thymidine kinase gene. In a particularly preferred embodiment, the adenoviral vector is Ad.HSV-tk. In another aspect of the invention, the expression vector is complexed with a nonviral vector. Preferably, this nonviral vector is a liposome or receptor ligand. Advantageously, the suicide compound is either ganciclovir or acyclovir and the modification is phosphorylation. In another aspect of this embodiment, the phosphorylated compound is further phosphorylated by cellular enzymes and is preferentially incorporated into the DNA of rapidly dividing cells.

The present invention also provides a recombinant adenoviral vector Ad.HSV-tk comprising:

a wild type adenovirus wherein the E3 region and about 9 map units have been deleted; and a HSV-tk expression cassette inserted into the deleted region, the expression cassette comprising the herpes simplex virus thymidine kinase gene operably linked to promoter, enhancer, encapsidation signal and origin of replication elements. Preferably, the wild type adenovirus is type 5 adenovirus and the elements are derived from polyoma virus and adenovirus.

In another aspect of the invention, there is provided a method for inhibiting restenosis associated with mechanical treatment of a blood vessel in a mammal comprising:

introducing a polynucleotide to the blood vessel after the mechanical treatment, the polynucleotide comprising a suicide gene that encodes a suicide protein;

expressing the suicide gene to produce the suicide protein in cells of said blood vessel; and administering a suicide compound to a mammal, wherein the proliferating cells are killed as a result of modification of the suicide compound by the suicide protein.

In another aspect of this embodiment, the mechanical treatment is balloon angioplasty, laser, atherectomy device or stent implantation. Preferably, the suicide gene is the thymidine kinase gene and the suicide protein is thymidine kinase. Advantageously, the suicide gene is contained within a eukaryotic expression vector, preferably a viral vector. In another aspect of this preferred embodiment, the viral vector is a retroviral vector; most preferably, it is an adenoviral vector. In another aspect of the invention, the eukaryotic expression vector containing the suicide gene may be complexed with nonviral vectors such as liposomes or receptor ligands. In preferred embodiments, the suicide compound is ganciclovir or acyclovir and is phosphorylated by the thymidine kinase. In a particularly preferred embodiment, the phosphorylated ganciclovir is preferentially incorporated into the DNA of rapidly dividing cells.

DETAILED DESCRIPTION OF THE INVENTION

Figure 1:
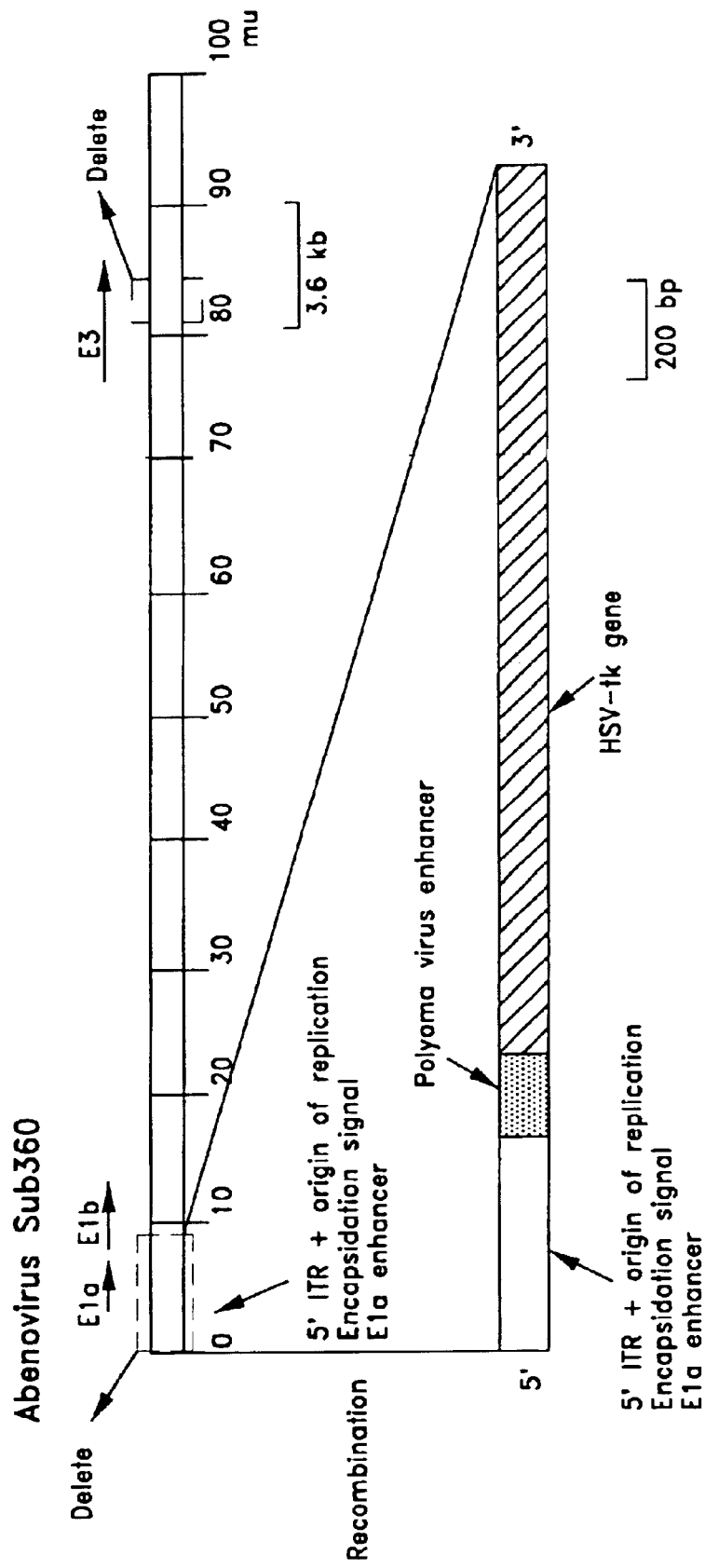
FIG. 1 depicts the construction of the recombinant Ad.HSV-tk adenoviral vector. The HSV-tk expression cassette containing the adenovirus 5' inverted terminal repeat (ITR), origin of replication, encapsidation signal and E1a enhancer is shown during insertion into a replication-deficient adenovirus.

The present invention provides a method for inhibiting the neointimal hyperplasia (restenosis) that occurs after balloon angioplasty. This method is practiced by directly introducing a suicide gene into the arterial lumen. The introduced gene is taken up and expressed in neighboring vascular smooth muscle and endothelial cells. Expression of the gene alone should have no effect on the cellular machinery. Once the suicide gene has been expressed, the mammal is treated with a suicide compound. If the suicide gene product and the suicide compound come together in a proliferating cell, the cell is killed. This method thereby provides an efficient treatment for specifically inhibiting restenosis of smooth muscle cells. As non-proliferating cells are not killed by the suicide gene, this method can be used to specifically kill any fast growing smooth muscle cells in a population of other cell types.

As used herein, the term "mechanical treatment" indicates any means of opening an occluded blood vessel. This might include, but is not limited to, balloon angioplasty, laser treatment, atherectomy device treatment and stent implantation. The term "mechanical injury" refers to the consequence of the "mechanical treatment". The term "suicide gene" refers to a gene whose protein product is capable of converting a suicide compound into a toxic product in the cell.

In a preferred embodiment, the suicide gene is in a eukaryotic expression vector. In a particularly preferred embodiment, the expression vector is in a replication-deficient adenoviral vector. These vectors can transduce nonproliferating cells, have not been shown to induce neoplastic transformation, can carry more than 7.5 kilobases of DNA and are common human pathogens that have been used for vaccination and gene therapy.

A wide variety of vehicles are available for delivering the suicide gene. A preferred method of delivering the adenoviral vector containing the suicide gene to the site of mechanical injury is through a catheter in solution. Alternatively, the gene may be complexed with nonviral vectors such as liposomes to facilitate fusion with the plasma membrane of the endothelial cells and smooth muscle cells lining the blood vessel. One method of liposome preparation involves, for example, use of the Lipofectin™ reagent (Gibco-BRL, Gaithersburg, Md.). The gene may also be conjugated to a receptor ligand such as transferring which will transport the gene to the cell surface and facilitate its entry into the cell by receptor-mediated endocytosis (Curiel et al., (1991) *Proc. Natl. Acad. Sci. USA*, 88:8850–8854.

In another preferred embodiment, the suicide gene encodes the HSV-tk protein. This gene encodes a viral protein, thymidine kinase, which is important in the synthesis of nucleic acid precursors normally within cells infected with herpes virus. This enzyme can phosphorylate the guanosine analog GCV, resulting in a GCV-monophosphate, in contrast to uninfected cells which contain a cellular thymidine kinase gene which does not act on this substrate. The GCV monophosphate is then phosphorylated by cellular protein kinases producing a GCV-triphosphate in cells which contain HSV-tk. The GCV-triphosphate is preferentially incorporated into the DNA of rapidly dividing cells, but, due to its chemical structure, cannot promote further elongation of the nascent DNA resulting in chain termination and cell death. The GCV may be administered either systemically or orally.

Any suicide gene that is capable of modifying a nontoxic compound into a toxic compound when expressed in vivo is within the scope of the present invention. For example, the bacterial enzyme cytosine deaminase converts the ordinarily nontoxic nucleoside analog 5-fluorocytosine to the cytotoxic 5-fluorouracil. Use of the β-glucosidase gene as a suicide gene is also contemplated.

Intravenous or intraarterial administration of the adenoviral HSV-tk construct is performed either immediately or soon after mechanical vessel injury. In a preferred embodiment, the amount of adenoviral vector administered is between about $10^6$ plaque forming units (pfu)/ml and about $10^{12}$ pfu/ml. In a particularly preferred embodiment, the amount of vector administered is $10^{10}$ pfu/ml. In another preferred embodiment, about 24–48 hours after administration of the retroviral vector to allow for transfection and expression of the tk gene, GCV is administered systemically twice a day for between about 4 and about 8 days. In a particularly preferred embodiment, GCV is administered 36 hours after vector administration for a period of six days. The amount of GCV administered will depend on the severity of the atherosclerotic obstruction, the health of the patient as well as other factors, but is generally in the range of about 10 mg/kg to about 100 mg/kg, preferably about 25 mg/kg to about 50 mg/kg.

The adenoviral vector encoding the HSV-tk gene is constructed as described in the following example.

EXAMPLE 1

Construction of HSV-tk Adenoviral Vector

The replication-deficient recombinant adenoviral vector Ad.HSV-tk was constructed by deleting the E3 region and 9.2 map units of the left end of the wild type adenovirus type 5 (Ad5) and adding to this end the HSV-tk expression cassette from the plasmid pAd-HSV-tk (FIG. 1). This expression cassette contains the HSV-tk gene, the polyoma virus enhancer, and the adenovirus inverted terminal repeat (ITR), encapsidation signal and E1a enhancer region.

Plasmid pAd-HSV-tk was constructed by introducing the HSV-tk gene (Mansour et al., (1988) *Nature*, 336:348–352) into the BglII site of pAd-BglII (Davidson et al., (1993) *Nature Genet.*, 3:219–223). Various DNA constructs encoding HSV tk genes are available from American Type Culture Collection, Rockville, Md., and include ATCC 39371, ATCC 39369 and VR-2036. To construct the recombinant adenoviral vector Ad.HSV-tk, pAd-HSV-tk was digested with NheI and cotransfected with XbaI- and ClaI-precut Sub360 DNA (Davidson et al., ibid.) into the human embryonic kidney cell line 293 (ATCC CRL 1573). Infectious virus was isolated by plaque purification and clones expressing the tk gene were selected by GCV treatment. For large preparation of viruses, Ad.HSV-tk and Ad5, E1a and E1b deletion mutant Ad. $\Delta$E1a and $\Delta$E1b were propagated in 293 cells, then purified by ultracentrifugation in a cesium chloride gradient.

The recombinant adenovirus was constructed by homologous recombination in 293 cells between plasmid pAd.HSV-tk and Ad.5 genomic DNA. Briefly, 293 cells were cotransfected with 5 $\mu$g linearized pAd.HSV-tk and 5 $\mu$g of digested Ad.5 DNA. After overlay with agar and incubation for 10 days at 37° C., plaques containing recombinant adenovirus were picked and screened for tk activity. Recombinant viral stocks were prepared in 293 cells. Cell pellets were resuspended in 10 mM Tris-HCl, pH 8.0, lysed by three rounds of freeze-thaw and centrifuged at 1,500×g for 20 minutes. Crude viral supernatants were centrifuged for 2 hours at 50,000×g in a cesium chloride gradient. Intact viral particles were subjected to a second round of cesium chloride purification resulting in 3–6×$10^{13}$ viral particles in 500–700 $\mu$l as measured by absorbance at 260 nm. Concentrated viral stocks were desalted by gel filtration on Sephadex G-50 in Hams F12 medium to yield a final purified stock of 1–2× $10^{12}$ viral particles/ml. Viral titers yielded stocks ranging from 0.2–2×$10^{12}$ pfu/ml. All stocks were evaluated for the presence of replication competent adenovirus by infection of HeLa cells at a multiplicity of infection of 10 and passaging the cells for 30 days. Since no cytopathic effect was observed in these cells, no replication competent virus was present.

EXAMPLE 2

Effect of HSV-tk Gene on Smooth Muscle Cells in vitro

To assess the efficacy of the HSV-tk gene on porcine vascular smooth muscle cells after exposure to GCV, these cells were infected in vitro with the adenoviral vector and exposed to GCV. Cells transfected with a control adenoviral vector lacking the tk gene (Ad.$\Delta$E1A) were entirely resistant to GCV, while cells transfected with Ad.HSV-tk were completely nonviable within 48 hours. Mixtures of transduced and nontransduced cells showed that when as few as 25% of the cells were transduced with Ad.HSV-tk, the untransfected cells were also affected by GCV treatment. Thus, this so-called "bystander effect", previously demonstrated in a variety of malignancies, was effective in the inhibition of vascular smooth muscle cells in vitro. This effect was also seen in porcine endothelial cells, as well as human vascular smooth muscle and endothelial cells.

Proliferation of intimal smooth muscle cells was measured in injured porcine arteries as described below.

EXAMPLE 3

Effect of Balloon Injury on Smooth Muscle Cell Proliferation in Porcine Arteries Domestic Yorkshire pigs (12–15 kg) were anesthetized with zolazepamin/tiletamine, 6.0 mg/kg, in combination with rompun, 2.2 mg/kg IM, with 1% nitrous oxide, intubated and subjected to sterile surgical exposure of the iliofemoral arteries. A double balloon catheter (C.R. Bard, Inc.) was inserted into the iliofemoral artery. The proximal balloon was inflated to a pressure of 500 mm Hg for 5 minutes. Animals were sacrificed at 1, 2, 4, 7, 14, 21 and 60 days following injury (n=2 animals per group). All animals received an intravenous infusion of 5-bromo-2'-deoxycytidine (BrdC, Sigma, St. Louis, Mo.), 25 mg/kg total dose 1 hour prior to sacrifice. BrdC, a thymidine analog, is incorporated into replicating DNA and is a marker of cell division.

Immunohistochemistry using a monoclonal anti-BrdC antibody was performed to label nuclei in proliferating cells. Artery segments were fixed in methyl Carnoy's solution, embedded in paraffin, sectioned at 6 $\mu$m, deparaffinized in three changes of xylene, and rehydrated in 100%, 95% and 75% ethanol. Endogenous peroxidase was blocked by preincubation in 0.3% hydrogen peroxide for 5 minutes. Sections were incubated in phosphate-buffered saline (PBS) containing 1% bovine serum albumin (BSA) with a 1:1000 dilution of a monoclonal anti-BrdC antibody (Amersham, Arlington Heights, Ill.) at room temperature for 60 minutes. The sections were rinsed in tris-buffered saline (TBS) and incubated in a 1:400 dilution of a biotinylated horse anti-mouse $IgG_2$ antibody (Zymed, South San Francisco, Calif.) for 30 minutes at room temperature. Specimens were rinsed in TBS and stained with a 1:5000 dilution of streptavidin horseradish peroxidase complex (Vector laboratories, Burlingame, Calif.) for 30 minutes at room temperature. After a final rinse in TBS, sections were incubated for 10 minutes at room temperature in a diaminobenzidine substrate (Sigma) in 0.045% nickel chloride to produce a gray-black reaction product. Methyl green nuclear counterstaining was also performed. Proliferation of intimal smooth muscle cells was assessed by counting the number of labeled and unlabeled nuclei in cross sections of all arteries, using a microscope-based video image analysis system (Image-1

System, Universal Imaging, Westchester, Pa.). Injured iliofemoral arteries and uninjured carotid arteries were examined in the same animal.

Figure 2:
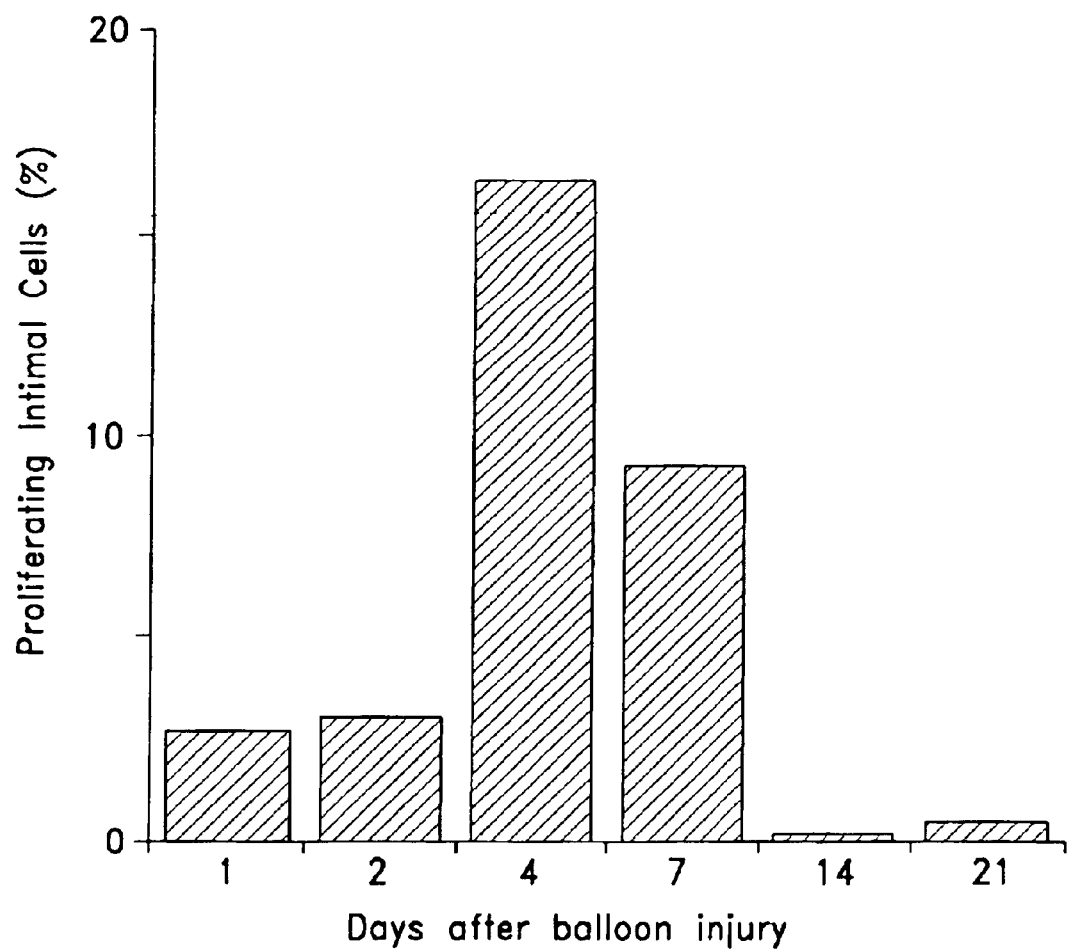
FIG. 2 shows the percentage of proliferating neointimal cells at various times after balloon injury in the porcine iliofemoral artery. The number of days after injury is shown on the x-axis and the percentage of proliferating cells is shown on the y-axis.

The results indicated that cell proliferation in the arterial intima was first evident approximately 24–48 hours after balloon injury to the iliofemoral artery (FIG. 2). Cell proliferation peaked at 4 days, continued for approximately 7 days following the injury and subsided by 14 days. Continued expansion of the arterial intima occurred in the absence of cell proliferation by deposition of increased matrix through 21 days post-injury. After this time, the proliferative response and intimal expansion were less severe.

The recombinant adenoviral vector encoding the HSV-tk gene was then transduced into mechanically injured porcine iliofemoral arteries as described below.

EXAMPLE 4

Balloon Injury and Adenoviral Transfection of Porcine Arteries

Domestic Yorkshire pigs were anesthetized and catheterized as described in Example 3. After inflation of the proximal balloon, the balloon was deflated and the catheter advanced so that the central space between the proximal and distal balloon now occupied the region of previous balloon injury. Both balloons were then inflated and the artery segment was irrigated with heparinized saline. In Group 1 (n=2, 4 arteries) and Group 2 (n=2, 4 arteries) animals, the recombinant adenoviral vector Ad.HSV-tk described in Example 1 was instilled ($10^{10}$ pfu/ml) for 20 min in the central space of the catheter. The catheter was removed and antigrade blood flow was restored. Group I animals were administered 25 mg/kg GCV twice daily by indwelling catheter into the internal jugular vein (7.5 ml total volume) for six days beginning 36 hours after the balloon injury and transfection, since the most active neointimal proliferation occurred between day 1 and day 7 after balloon injury (FIG. 2). Group 2 animals received intravenous saline in an equivalent weight adjusted volume to Group 1.

Additional control experiments included Group 3 and 4 animals in which balloon injury of the porcine iliofemoral arteries was performed, followed by transfection with an E1a-deleted adenovirus (Ad.ΔE1a) which did not contain a HSV-tk gene. Group 3 animals received GCV, while Group 4 received saline in equivalent doses to Groups 1 and 2. Animals were sacrificed at day 21 and the artery segments excised.

Inhibition of neointimal hyperplasia was assessed as described in the following example.

EXAMPLE 5

Assay of Neointimal Hyperplasia

Each iliofemoral artery was cut into five cross-sectional pieces. Two sections were fixed in methyl Carnoy's, while two sections were fixed in formalin. All four sections were embedded in paraffin. One section was frozen in liquid nitrogen and stored at −80° C. for DNA isolation.

Since smooth muscle cells migrate from the media to the intima upon proliferation, the determination of the intima/media thickness ratio indicates the extent of hyperplasia occurring after balloon injury. Measurements of intimal and medial area were determined in a blinded manner. Slides of arterial specimens were studied with a microscope based video imaging analysis system (Image-1 System, Universal Imaging, Westchester, Pa.). Images were digitized, intimal and medial regions were traced and areas were calculated. In each artery, four cross sections were calculated and intimal and medial thickness ratios were calculated. Comparisons of intimal and medial thickness, and intimal to medial ratios between the four groups of animals were made by analysis of variance with Dunnett's test. Statistical significance was accepted at the 95% confidence level.

Figure 3:
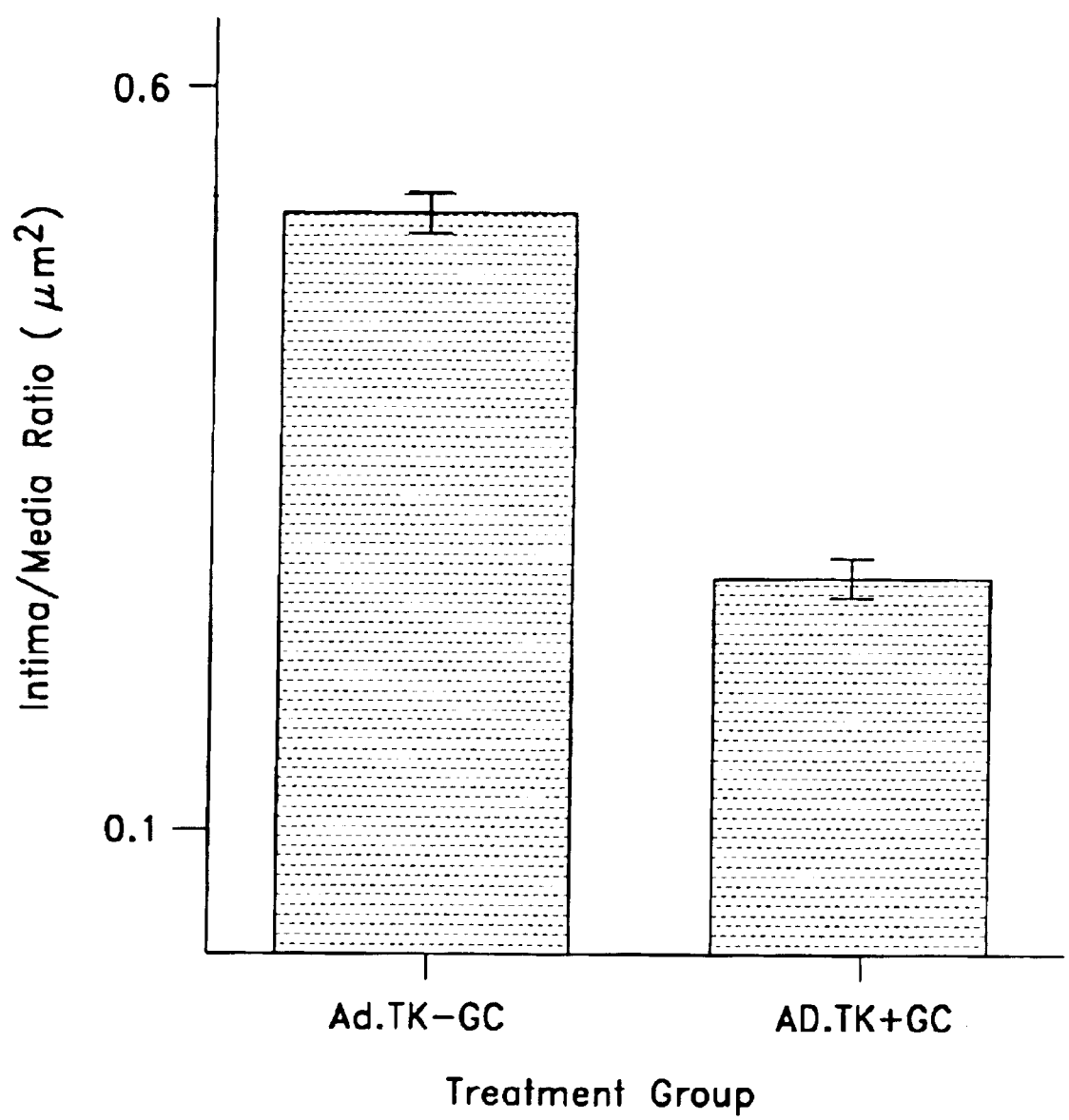
FIG. 3 shows the inhibition of vascular smooth muscle cell proliferation in porcine iliofemoral arteries transfected with the recombinant Ad.HSV-tk adenoviral vector. The presence or absence of GCV treatment is shown on the x-axis and the intima/media ratio, an indicator of vascular smooth muscle cell proliferation, is shown on the y-axis.

Quantitative morphometric analysis of artery specimens from groups 1–4 revealed a significant reduction in intimal to medial thickness in Ad.HSV-tk+GCV animals (Group 1) compared with Ad.HSV-tk−GCV (Group 2), Ad.ΔE1a+GCV (Group 3) and Ad.ΔE1a−GCV (Group 4) animals (all $p<0.05$). The results indicate that adenoviral transfection of the HSV-tk gene and treatment with GCV produces a 50% inhibition of intimal smooth muscle cell proliferation in vivo (Ad.TK−GC vs. AD.TK+GC; FIG. 3). These values were significant since the unpaired two-tailed T-test indicated a P value of 0.01. In contrast, no difference was noted between animals which received the E1a-deleted adenoviral vector, regardless of whether or not they were treated with GCV.

To assess the toxicity of adenoviral vectors in porcine arteries, the E1a-deleted adenovirus was transfected into uninjured porcine arteries as described below.

EXAMPLE 6

Toxicity of Adenoviral Vectors in Porcine Arteries

The E1a-deleted adenovirus was transfected into uninjured porcine arteries at $10^9$ pfu/ml (n=2) and $10^{10}$ pfu/ml (n=2) as described in Example 4. Analysis of arterial cross sections at three weeks by light microscopy revealed no evidence of inflammation or necrosis. Intimal and medial thickening were not present compared with untreated controls as assessed by quantitative morphometry. Nontransfected tissues from these animals including brain, heart, lung, liver, kidney, spleen, skeletal muscle, ovary and testes were analyzed by light microscopy for organ pathology and by serum biochemical analysis for enzyme abnormalities. No changes were noted in these parameters. Moreover, adenoviral DNA was not observed in these tissues as determined by polymerase chain reaction. Thus, in vivo toxicities of the quantities of intraarterially administered adenoviral vector used for this treatment were minimal.

EXAMPLE 7

Prevention of Neointimal Hyperplasia in Humans

After undergoing balloon angioplasty, the patient is administered the Ad.HSV-tk adenoviral vector described in Example 1 by instillation of $10^8$ to $10^{12}$ pfu/ml instilled through the catheter within the artery. After 36 hours, patients are intravenously administered between 10 mg/kg and 100 mg/kg GCV at twelve hour intervals for 4 to 8 days. Since the intimal thickening associated with balloon injury may progress at a different rate than in the porcine artery, the number of days of GCV administration may need to be adjusted, although the porcine profile of intimal thickening is most likely very similar to that of a human. The efficacy of the treatment is assessed by an angiogram months after the procedure.

We claim:

1. A method for inhibiting vascular smooth muscle cell proliferation after balloon injury of a blood vessel in a mammal, comprising:

introducing a polynucleotide to said blood vessel by catheter instillation at the site of said balloon injury after said balloon injury, said polynucleotide comprising a thymidine kinase gene in a eukaryotic expression vector complexed with a nonviral vector;

expressing said thymidine kinase gene to produce thymidine kinase protein in smooth muscle cells of said blood vessel; and then administering to said mammal an effective amount of a DNA replication-inhibiting nucleoside analog capable of being phosphorylated by said thymidine kinase protein, whereby said phosphorylated analog is preferentially incorporated into the DNA of proliferating cells, and whereby said proliferating cells are killed.

2. The method of claim 1, wherein said nonviral vector is a liposome.

3. The method of claim 1, wherein said nonviral vector is a receptor ligand and said expression vector-ligand complex binds to the receptor.

4. The method of claim 1, wherein said eukaryotic expression vector is a viral vector.

5. The method of claim 1, further comprising a polyoma virus enhancer upstream of said thymidine kinase gene.

6. The method of any one of claim 1, 2, 3, 4 or 5, wherein said nucleoside analog is ganciclovir or acyclovir.

7. The method of claim 6, wherein said phosphorylated analog is further phosphorylated by intracellular enzymes.

* * * * *